(12) United States Patent
Koizumi et al.

(10) Patent No.: US 7,438,706 B2
(45) Date of Patent: Oct. 21, 2008

(54) AUTOMATIC URINE COLLECTING APPARATUS

(75) Inventors: Hiroshi Koizumi, Tokyo (JP); Ryosuke Miyakawa, Tokyo (JP); Yoshikazu Ishizuka, Ibaraki (JP); Tetsuya Tanaka, Ibaraki (JP); Shigeharu Sayama, Fukuoka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/244,183

(22) Filed: Oct. 6, 2005

(65) Prior Publication Data

US 2006/0084932 A1    Apr. 20, 2006

(30) Foreign Application Priority Data

Oct. 20, 2004    (JP)    ............................ 2004-305316
Jul. 26, 2005    (JP)    ............................ 2005-216252

(51) Int. Cl.
*A61M 1/00* (2006.01)

(52) U.S. Cl. ...................... 604/327; 604/317; 604/540

(58) Field of Classification Search ......... 604/327–332, 604/346–350
See application file for complete search history.

(56) References Cited

U.S. PATENT DOCUMENTS 2,749,558 A    6/1956    Lent et al.
3,112,061 A    11/1963    Breer
4,631,061 A    12/1986    Martin et al.
6,526,603 B1    3/2003    Murphy
6,706,027 B2 *    3/2004    Harvie ........................ 604/347

FOREIGN PATENT DOCUMENTS

| JP | 8-505061 | 6/1996 |
| JP | 8-510924 | 11/1996 |
| JP | 2000-152953 | 6/2000 |
| WO | 93/09736 | 5/1993 |
| WO | 94/03214 | 2/1994 |

* cited by examiner

*Primary Examiner*—Michele Kidwell
(74) *Attorney, Agent, or Firm*—Mattingly, Stanger, Malur & Brundidge, P.C.

(57) ABSTRACT

An automatic urine collecting apparatus for collecting urine received by a urine receiver through a tube, includes: a container for receiving and storing urine; a pump that sucks and conveys urine from the urine receiver to the container through the tube, wherein the pump comprises a rotary pump. A body including the pump may cover an opening of container. An overhead portion included in the body may cover the opening of container. The apparatus may further comprise an elevator mechanism to elevate the container to couple the container to the overhead portion.

12 Claims, 11 Drawing Sheets

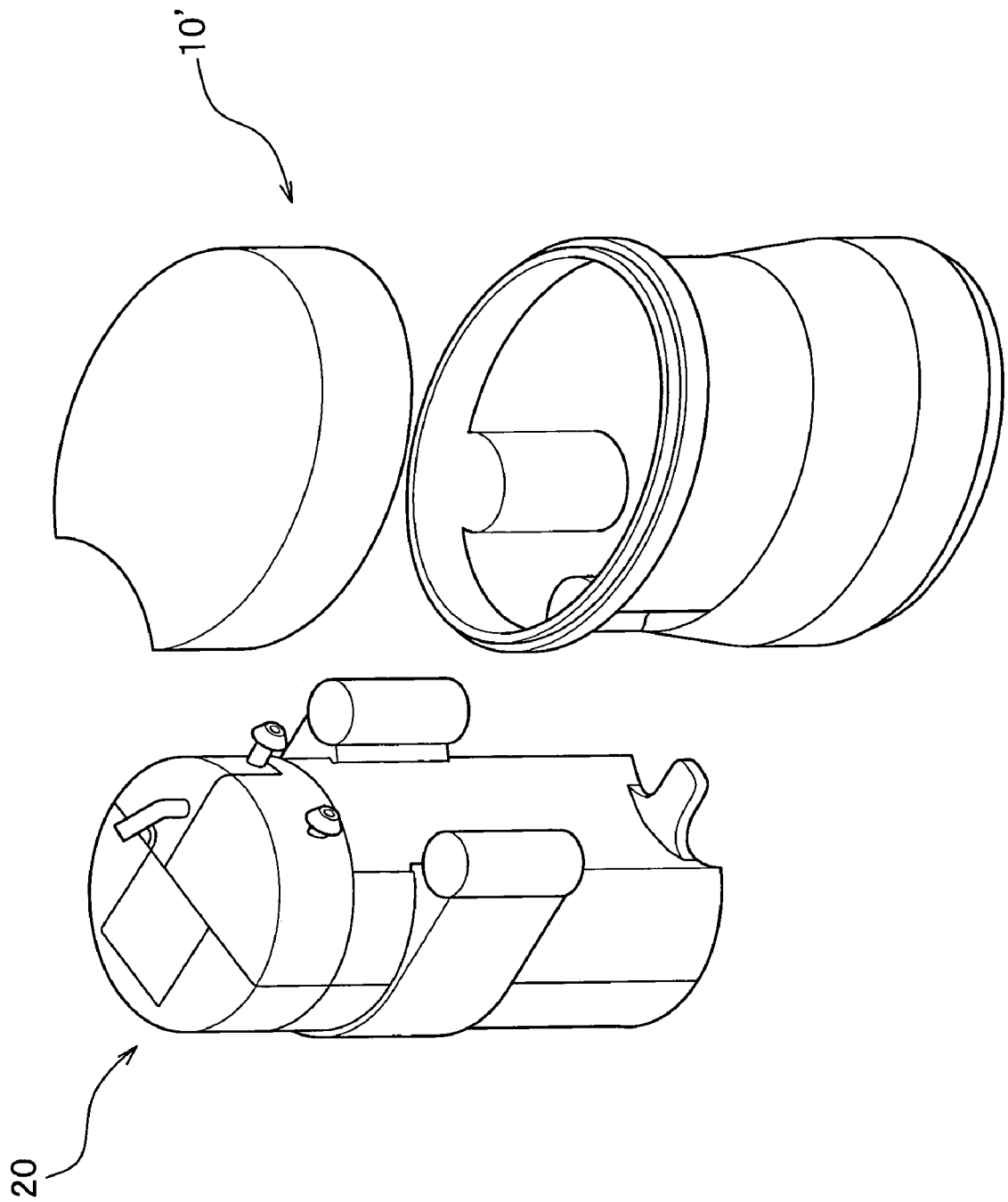

AUTOMATIC URINE COLLECTING APPARATUS

FIELD OF THE INVENTION

The present invention relates to an automatic urine collecting apparatus for automatically collecting evacuated urine.

BACKGROUND OF THE INVENTION

Automatic urine collecting systems for automatically collecting urine evacuated by a bedridden person or an aged human being are known. The automatic urine collecting system includes a urine receiver attached to a waist portion of a patient with a diaper, a tube connected to the receiver at one end, and an automatic urine collecting apparatus connected to the other end of the tube. Japanese laid-open patent application publication No. 2000-152953 discloses such a liquid removal system which includes a collecting container for storing liquid evacuated from the receiver through the tube and a suction pump for sucking and conveying liquid in the receiver to the collecting container.

SUMMARY OF THE INVENTION

An aspect of the present invention provides an automatic urine collecting apparatus comprising as a suction pump a rotary pump with a superior suction power, in which sound noise is suppressed and the size of the apparatus is reduced.

Another aspect of the present invention provides an automatic urine collecting apparatus for collecting urine received by a urine receiver through a tube, the apparatus comprising: a container for receiving and storing urine; a pump generates a reduced-pressure to suck and convey urine from the urine receiver to the container through the tube, wherein the pump comprises a rotary pump.

A further aspect of the present invention provides an automatic urine collecting apparatus for collecting urine received by a urine receiver through a tube, the apparatus comprising: a container for receiving and storing urine; a pump for generating a reduced-pressure to suck and convey urine from the urine receiver to the container through the tube and the container, wherein the pump, the container, and the tube and the receiver are hermetically sealed.

BRIEF DESCRIPTION OF THE DRAWINGS

The object and features of the present invention will become more readily apparent from the following detailed description taken in conjunction with the accompanying drawings in which:

FIG. 6 is an exploded perspective view of another example of an automatic urine collecting apparatus according to the first embodiment;

The same or corresponding elements or parts are designated with like references throughout the drawings.

DETAILED DESCRIPTION OF THE INVENTION

First Embodiment

Figure 1:
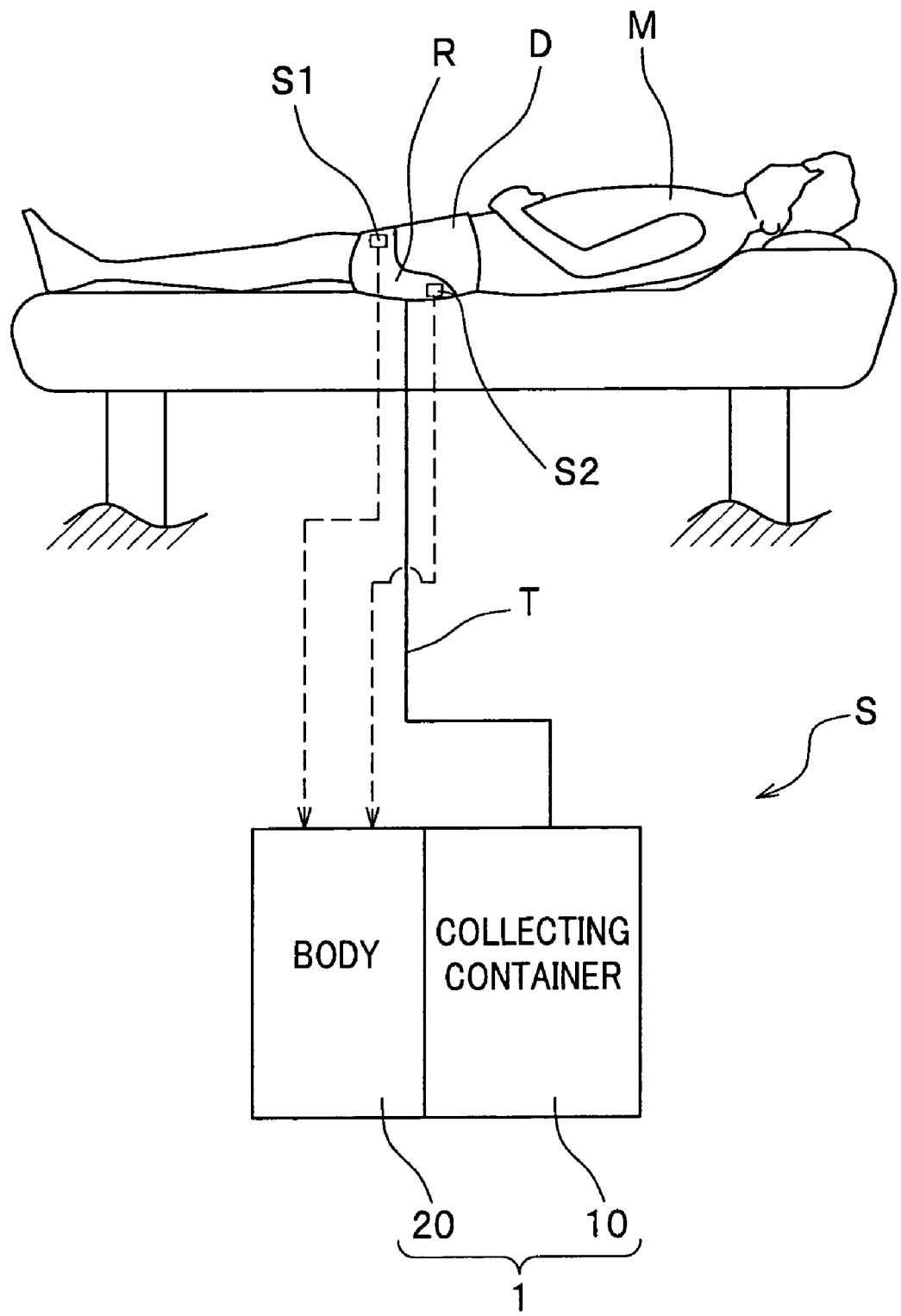
FIG. 1 is a block diagram of an automatic urine collecting system according to the present invention.
Figure 2B:
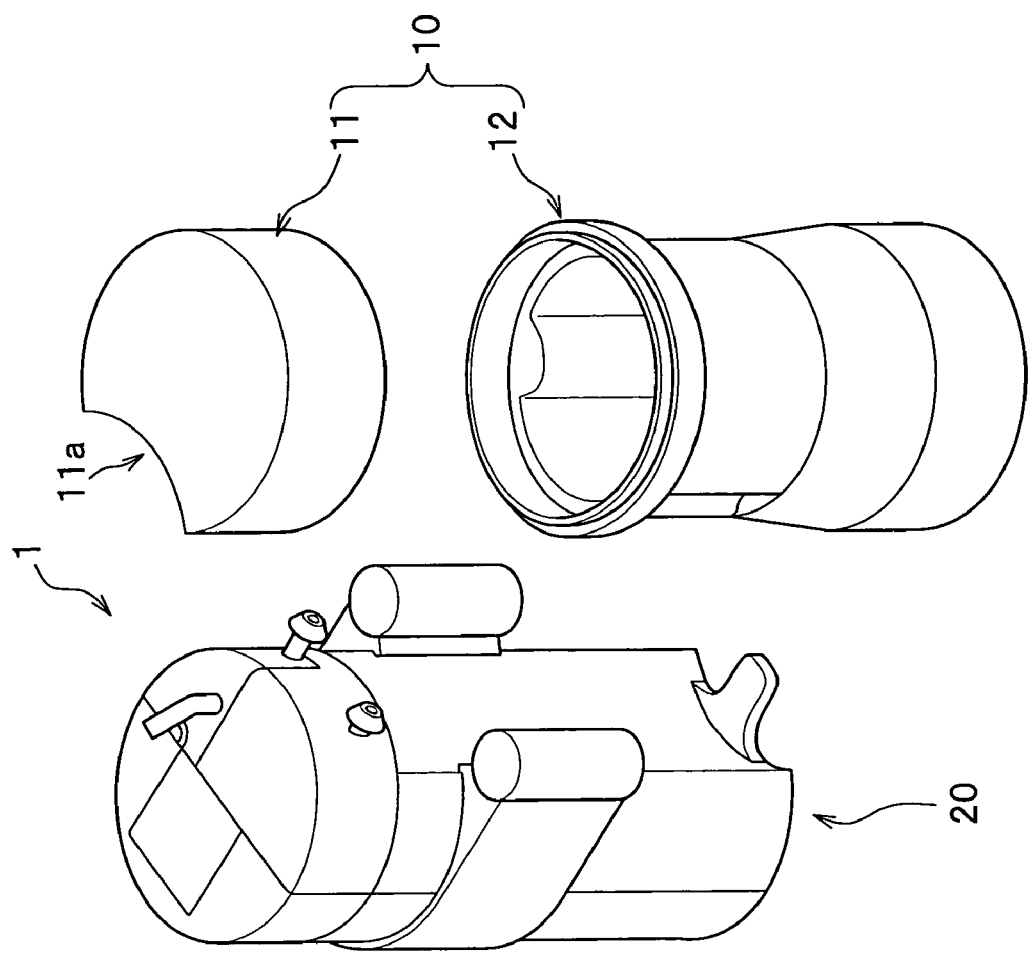
FIG. 2B is an exploded perspective view of the automatic urine collecting apparatus according to the first embodiment.
Figure 2A:
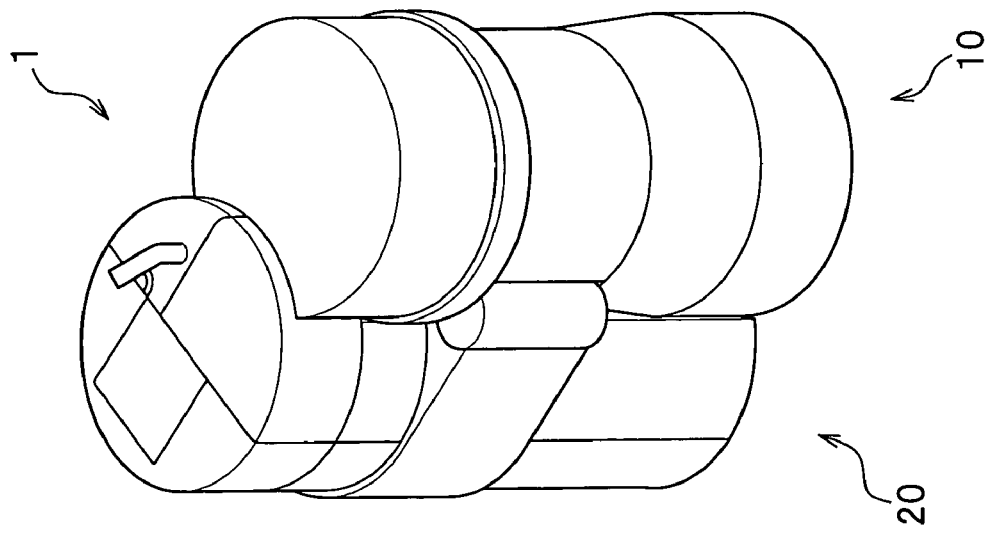
FIG. 2A is a perspective view of an automatic urine collecting apparatus according to a first embodiment.

A first embodiment of the present invention will be described with reference to drawings. FIG. 1 shows an automatic urine collecting system according to the present invention. FIG. 2A shows an automatic urine collecting apparatus 1 of the first embodiment that is used in the automatic urine collecting system shown in FIG. 1. FIG. 2B shows parts of the automatic urine collecting apparatus 1.

The automatic urine collecting system S comprises a urine receiver R attached to a diaper D and the automatic urine collecting apparatus 1 for automatically collecting urine received by the urine receiver R through a tube T. Provided in the diaper D are a urine sensor S1 for sensing the urine evacuated from a patient M and an excrement sensor S2 for sensing excrement evacuated by the patient M. Signals from the urine sensor S1 and the excrement sensor S2 are transmitted to the automatic urine collecting apparatus 1. For the urine sensor S1 and the excrement sensor S2, the same water detectors are used, but the urine sensor S1 and the excrement sensor S2 are distinctively used between the urine and excrement by differentiating their contact locations to the patient M.

Figure 4:
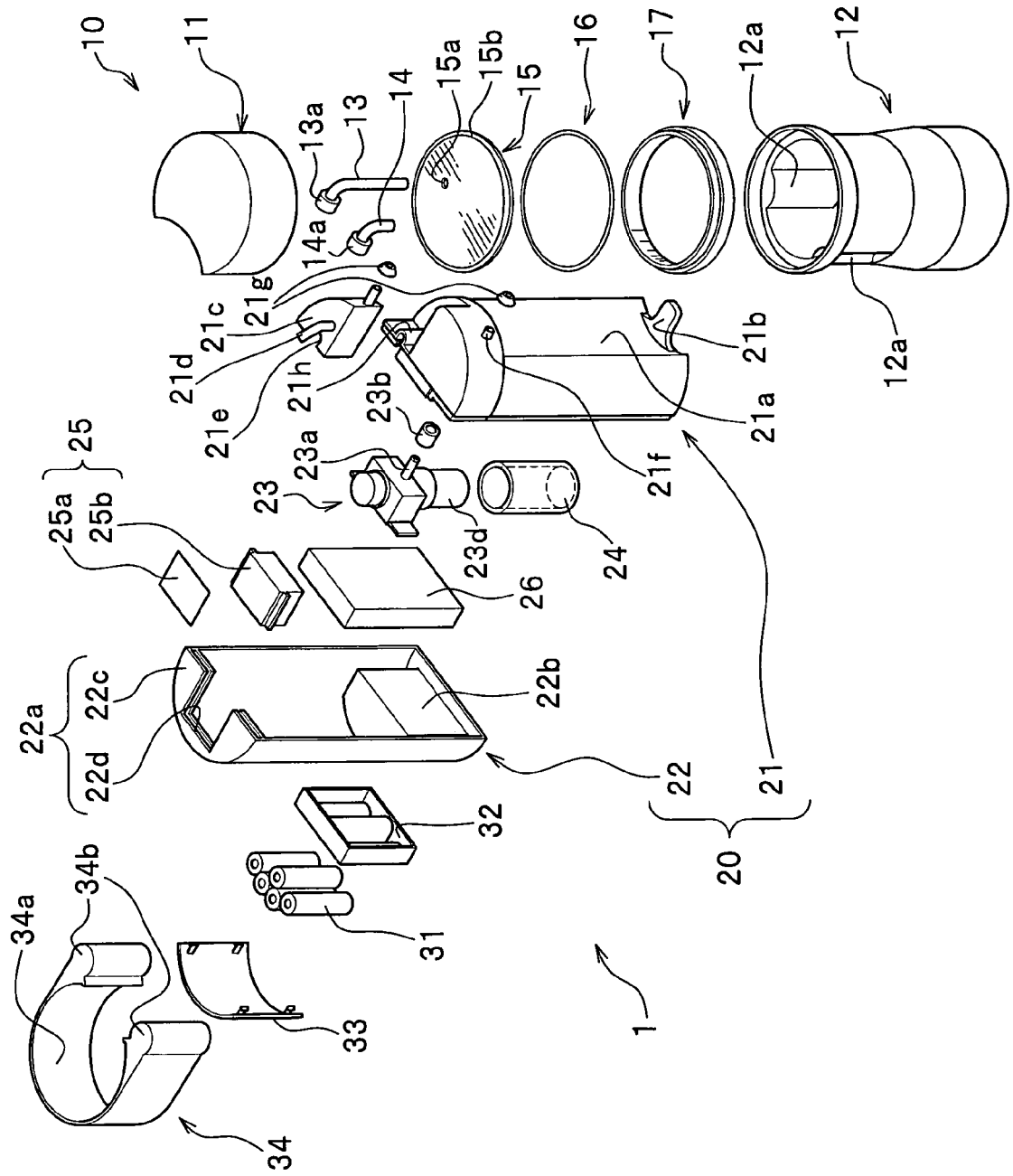
FIG. 4 is an exploded perspective view of the automatic urine collecting apparatus according to the first embodiment.

The automatic urine collecting apparatus 1 comprises a collecting container 10 for storing the urine conveyed from the urine receiver R through the tube T, a rotary pump 23 (see FIG. 4) for sucking and conveying the urine received by the urine receiver R to the collecting container 10. Both of the collecting container 10 and the body 20 are cup-shaped. The collecting container 10 is detachably attached to a side surface of the body 20.

The rotary pump 23 sucks a gas or a liquid from its inlet by rotating a pair of rotors and emits it at its outlet, continuously and has a relatively large suction force with a relative small size, wherein the sound noise is low. The rotary pump 23 may comprise an axial flow pump and a centrifugal pump.

The collecting container 10 comprises a lid portion 11 and a tank 12.

Figure 3:
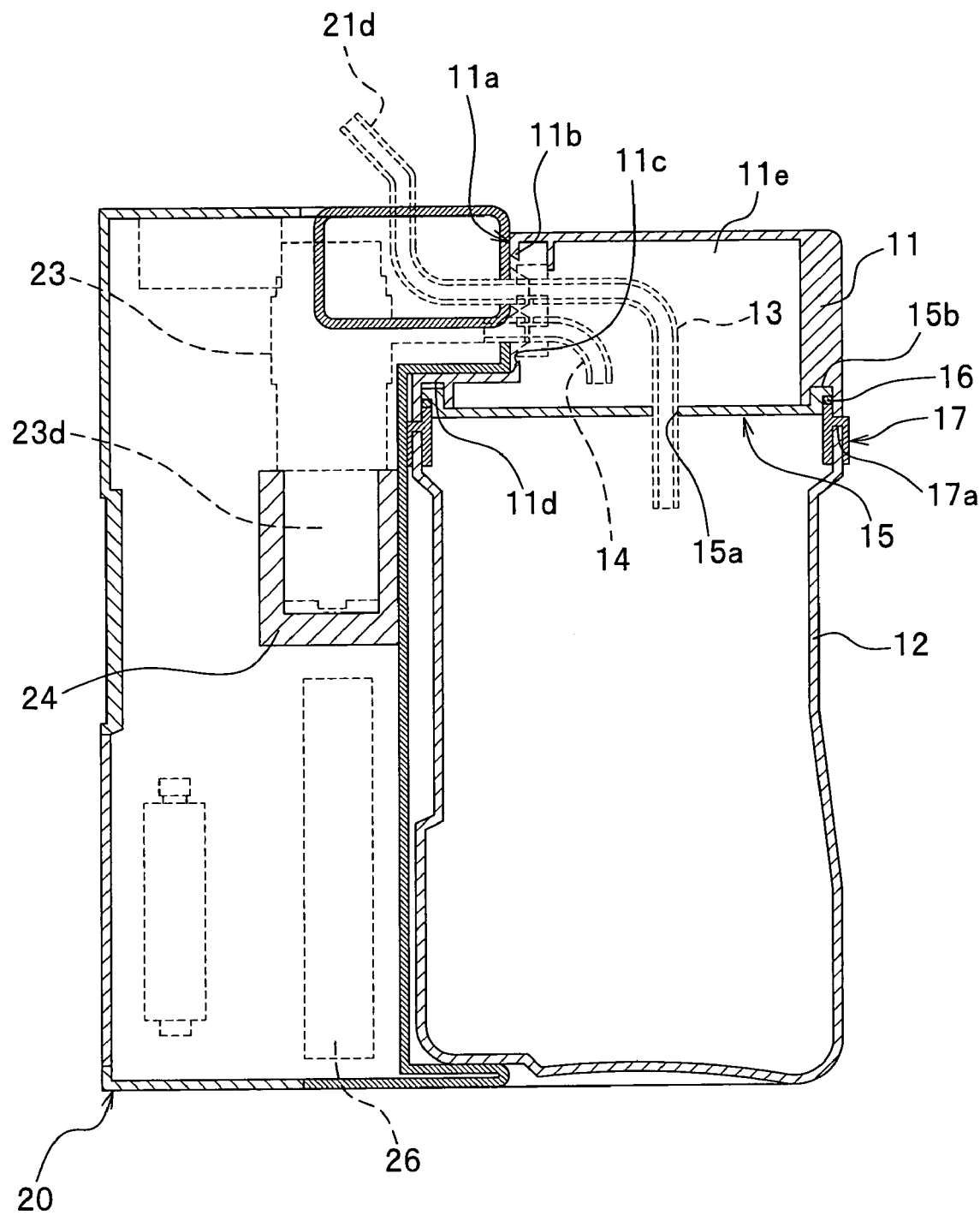
FIG. 3 is a section view of the automatic urine collecting apparatus according to the first embodiment.

The lid portion 11 is cup-shaped and has a clearance portion 11a fitting an outer circumferential shape of an upper portion of the body 20. The clearance portion 11a is formed by forming a portion of the lid portion 11 stepwise, as shown in FIG. 3. Provided within the lid portion 11 are a collecting pipe 13, a suction pipe 14, a gas-liquid separation filter 15, and an O ring 16.

The collecting pipe 13 is formed in a substantially L-shape and has a base end 13a which is fixed to an opening 11c in a vertical wall 11b of the clearance portion 11 so that the other tip end downwardly extends.

The suction pipe 14 is substantially L-shaped, of which one end downwardly extending in a chamber lie in the lid portion 11, is shorter than the corresponding portion of the collecting pipe 13. A base end 14a of the suction pipe 14 is fixed to the wall of the lid portion 11, i.e., the opening 11c in a vertical wall 11b of the clearance portion 11 so that the other end downwardly extends.

The gas-liquid separation filter 15 stops liquid passing therethrough and allows gas to pass therethrough and has a substantially circle shape. The gas-liquid separation filter 15 has a through hole 15a therein allowing the collecting pipe 13 to penetrate it at a suitable location and a stepwise rib 15b formed at a circumference of the gas-liquid separation filter 15. The stepwise rim 15b is fit into an annular recess lid (see FIG. 3) formed in a lower surface of a vertical wall of the lid portion 11 to fix the gas-liquid separation filter 15 to the lid portion 11. Located above the gas-liquid separation filter 15 is an end opening of the suction pipe 14. This prevents the liquid in the tank 12 from entering the suction pipe 14, when the rotary pump 23 sucks air in the tank 12.

The O ring 16 is formed to have a predetermined diameter and a predetermined thickness (sectional diameter) so as to be fit in the recess configured with the stepwise rim 15b of the gas-liquid filter 15 and the recess 11d of the lid portion 11.

The tank 12 is cup-shaped with a predetermined depth and has fitting recesses 12a at two locations on a side surface thereof to allow fitting portions 34b at a fitting arm 34 mentioned later at a side of the body 20 to fit in the fitting recess 12a. Provided at an upper edge of the tank 12 is an upper edge forming member 17. More specifically, the upper edge forming member 17 has a recess 17a formed underneath it and is fixed to the tank 12, in which the upper edge of the tank 12 is fit into the recess 17a. Thus, although the upper edge of the tank 12 is not horizontally formed by blow molding, i.e., the upper edge is formed roughly, use of the upper edge forming member 17 which is formed by a method other than the blow molding can secure a sealing property by evenly pressing the upper edge on the O ring 16. The material of the tank 12 is preferably polycarbonate. However, the material is changeable.

The upper edge of the upper edge forming member 17 can be detachably fit into the recess configured with the stepwise rim 15b of the gas-liquid separation filter 15 and the recess portion 11d of the lid portion 11. This allows the upper edge forming member 17 and the stepwise rim 15b of the gas-liquid separation filter 15 to pinch an open edge of a not-shown bag (holder) to support it, wherein the bag contains, for example, a not-shown absorbing material (polymer) for absorbing the urine. In other words, the collecting container 10 has a structure capable of attaching the bag containing the absorbing agent in which the lid portion 11 is fit to the upper edge of the tank 12. Attachment of the bag containing the absorbing agent to the collecting container 10 can suppress sound generated by drops evacuated from the collecting pipe 13 and then hitting an inner surface of a bottom of the tank 12 as well as if the tank 12 falls down, the urine does not poor out. Further, if a deodorant (not shown) is contained in the bag in addition to the absorbing agent, order can be absorbed by the deodorant.

The body 20 comprises two halves 21 and 22 formed such that the body 20 is divided along its vertical center plane into halves 21 and 22 and contains a rotary pump 23, a vibration absorber 24, an indication panel 25, and a control circuit board 26. For convenience of explanation, the half 21 at the side of the collecting container 10 is also referred to as "a front side half 21", and the half 22 on the opposite side is referred to as "a rear side half 22."

The front side half 21 has a clearance recess 21a formed in a half pipe having a diameter that is substantially the same as a maximum diameter of the tank 12. From a lower end of the clearance recess 21a, a supporting chip 21b for supporting the tank 12 extends along a bottom of the tank 12 toward the center of the bottom. A part of an upper portion of the front side half 21 is a separable portion 21c detachable from the front side half 21 and has the guide pipe 21d for guiding the urine evacuated by the tube T (see FIG. 1) into the collecting pipe 13 and a groove 21e allowing wirings to pass therethrough to transmit the signals from the sensors S1 and S2 to the control circuit board 26. In fact, because the groove 21e fits a half pipe 21h formed in the front side half 21, a path of the wirings is formed with the half pipe 21h of the front half 21 and the rear side half 22.

Another part of the upper portion of the front side half 21 opposite to the separable portion 21c is provided with the rotary pump 23 and a connecting pipe 21f for connecting the rotary pump 23 to the suction pipe 14. On tips of the connecting pipe 21f and the guide pipe 21d (an end at the side of the tank 12) intervening members 21g are mounted to connect the connecting pipe 21f to the suction pipe 14 and the guide pipe 21d to collecting pipe 13 hermetically.

Further, hermetical sealing (not shown) may be done around and within the opening 11c.

The rear side half 22 is formed to have, at an upper portion thereof, a mounting portion 22a for mounting an indication panel 25 and, at a lower portion thereof, a battery box 22b for containing batteries 31. More specifically, the mounting portion 22a is provided by forming a notch 22d corresponding to the indication panel 25 in the planer portion 22c including a groove in an edge surrounding the notch. The battery box 22b is formed by recessing a side surface of the rear side half 22 inwardly. Provided inside the battery box 22b are a plurality of dry batteries and an electrical connecting portion 32 for electrically connecting these dry batteries 31 to supply a power to the rotary pump 23, the indication panel 25, and the control circuit board 26. An opening of the battery box 22b is closed with a cover 33.

Provided at a substantially middle of the rear side half 22 is the fitting arm 34 formed in a substantially U-shape in a top view. More specifically, the fitting arm 34 comprises a U-shaped body 34a for pinching both the rear side half 22 and the front side half 21 and a cylindrical fitting members 34b for fitting into the above-mentioned fitting recess 12a of the tank 12.

The rotary pump 23 is a pump for sucking air in the tank 12 by rotating a pair of rotors inside thereof by a motor portion 23d integrally connected to a lower end of the rotary pump 23 to provide a large suction force with a relatively small size in which driving sound is low. A sucking inlet 23a of the rotary pump 23 is connected to the connecting pipe 21f through a rubber (elastic material) pipe 23b as well as the motor portion 23d is connected to a side wall of the body 20 through a rubber vibration absorber (elastic material) 24 (see FIG. 3). Accordingly, noise and vibration generated at the rotary pump 23 (pump mechanism at the upper side and the motor portion 23d at the lower side) is absorbed by the rubber pipe 23b and the vibration absorber 24.

Figure 5:
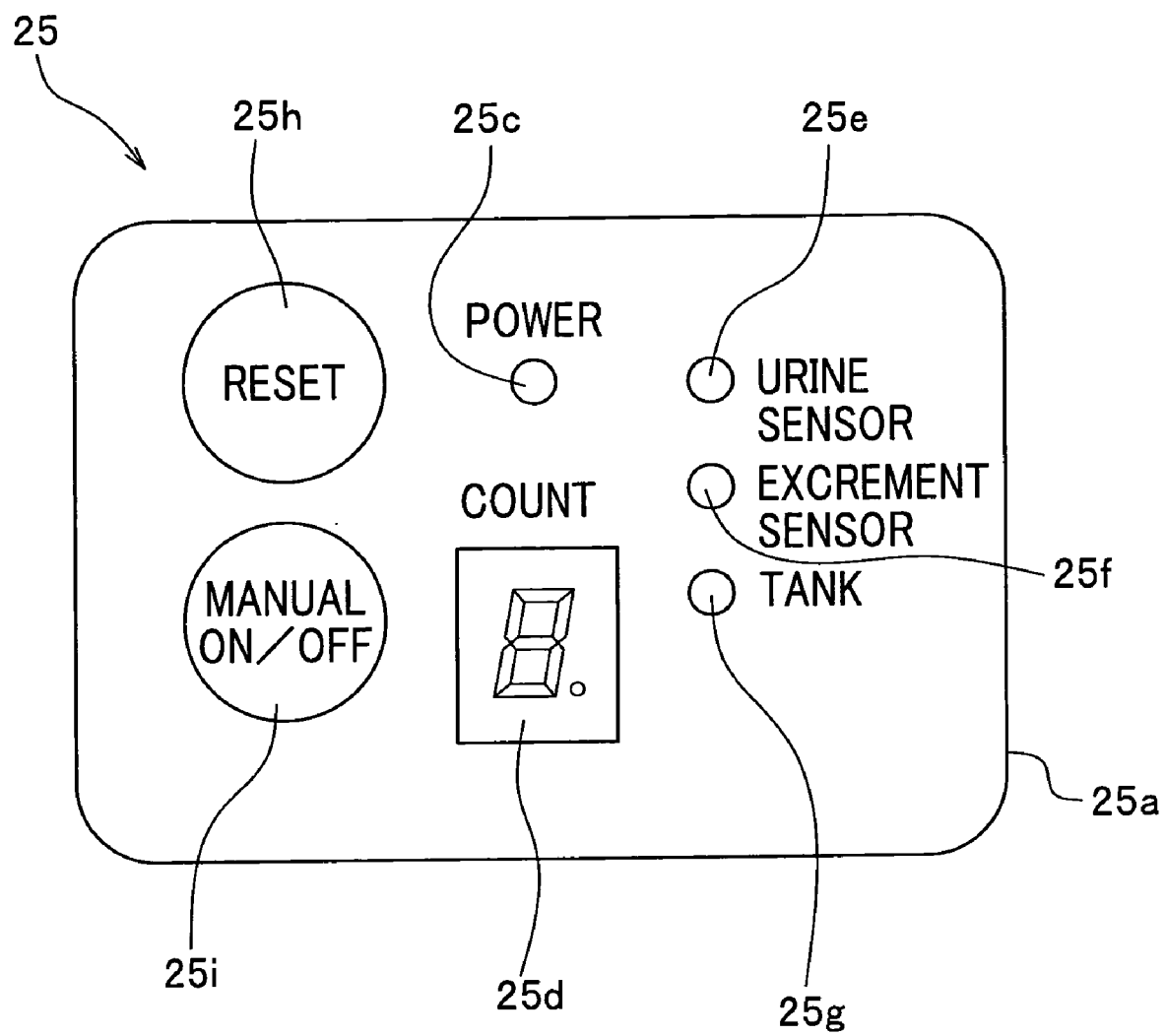
FIG. 5 is a plan view of an indication panel shown in FIG. 4.

The indication panel 25 comprises an operation panel 25a and a switch circuit board 25b. The operation panel 25a is, as shown in FIG. 5, a sheet of which surface is marked with characters, has transparent windows, and is adhered on an upper surface of the switch circuit board 25b. Provided on the circuit board 25b are switches, a display, and lamps, corresponding to the characters on the operation panel 25a. More specifically, the switch circuit board 25b comprises a lamp 25c indicating an ON/OFF status of the power, a display element 25d indicating the number of collecting urine (counts), a lamp 25e indicating an operation status of the urine sensor S1, a lamp 25f indicating an operation status of the excrement sensor S2, a lamp 25g indicating an exchanging timing of the tank 12, a reset switch 25h for resetting the number on the display element 25d and for turning off the lamps, and a drive switch 25i for manually driving the rotary pump 23. The lamp 25g indicting the exchanging timing of the tank 12 corresponding to "information for prompting discarding the urine stored in the collecting container" and configured to turn on, in this embodiment, when the urine collected three times in the tank 12. The lamps on the circuit board 25 and the display element 25d can be monitored through the transparent windows of the indication panel 25. The switches are depressed through the display panel 25a.

The control circuit board 26 controls units in this apparatus on the basis of the signals transmitted from the indication panel 25, the urine sensor S1, and the excrement sensor S2. More specifically, when the signal is transmitted from the urine sensor S1, the control circuit board 26 determines that urine is evacuated from the patient M to collect the urine in the tank 12 by driving the rotary pump 23 for a predetermined interval. When receiving the signals from both of the urine sensor S1 and the excrement sensor S2, the control circuit board 26 determines that a liquid detected by the urine sensor S1 is that of excrement (not urine) and thus allows the rotary pump 23 to stop. In addition, the control circuit board 26 further has a function for increasing the frequency of displaying the count on the display element (display window) 25d whenever the rotary pump 23 is driven for a predetermined interval and for driving the rotary pump 23 in response to the signal from the driving switch 25i.

Will be described an operation of the automatic urine collecting apparatus 1 with reference to FIGS. 1 to 4.

As shown in FIG. 1, when the patient M evacuates urine, the urine sensor S1 detects water in the urine and transmits the signal to the body 20. When receiving the signal from the urine sensor S1, the control circuit board 26 drives the rotary pump 23 for the predetermined interval. Alternatively, the rotary pump 23 may be stopped in response to the signals from the urine sensor S1.

The driven rotary pump 23 sucks the air in the tank 12 through the gas-liquid separation filter 15 and the suction pipe 14, decreasing a pressure in the tank 12. Decrease in the pressure in the tank 12 sucks the urine from the urine receiver R and conveys the urine to the tank 12 through the collecting pipe 13, the guide pipe 21d, and the tube T.

In this operation, the use of the rotary pump 23 can increase a performance of sucking the urine because the rotary pump 23 has a large suction force with a small size, so that driving sound is low and a total size of the automatic urine collecting apparatus 1 can be reduced.

Detachably attachment of the collecting container 10 facilitates discarding the urine. Further, when the bag containing the absorbing agent is attached in the collecting container 10, it is easier to discard the urine because it is enough to discard the bag including the urine.

The indication panel 25 that indicates the information prompting to discard the urine stored in the tank 12 is provided at the upper portion of the body 20. This eliminates necessity to watch inside of the tank 12 as the attendant bends down to know how mach urine has been stored in the tank 12, reducing a load on the attendant.

The attachment of the rotary pump 23 through the rubber pipe 23b and the vibration absorber 24 to the body 20 further reduces the driving sound.

The suction of the air in the tank 12 through the gas-liquid separation filter 15 can expand the life of the rotary pump 23 because the gas-liquid separation filter 15 prevents any liquid from entering the rotary pump 23.

The separable member 21c having the guide pipe 21d for guiding the urine is dividable from the front side half 21, so that only the separable portion 21c can be cleaned after the separable portion 21c is removed from the body 20. This prevents the rotary pump 23 from failing due to water entering its inside while the body 20 is being cleaned, expanding the life of the rotary pump 23.

The present invention can be carried out in various modes without limitation described in the above-mentioned first embodiment.

In the first embodiment, the collecting container 10 is formed in the substantially circle in the plan view. However, the present invention is not limited to this, but the collecting container 10 may be formed, for example, in a substantially oval in the plan view as shown in FIG. 6. Further, if two collecting containers 10 and 10' are prepared, preferably, the collecting container 10' with a large capacity is for night-use, and the collecting container 10 with a low capacity is for day-use to efficient use the apparatus. In this case, preferably, a capacity of the large collecting container 10' is about 1.5 litters, and a capacity of the small collecting container 10 is about one litter.

Second Embodiment

Figure 7C:
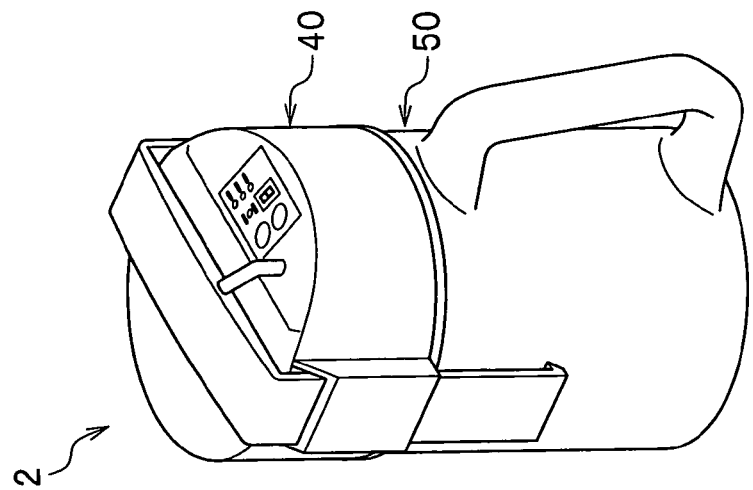
FIG. 7C is a perspective view of the automatic urine collecting apparatus shown in FIG. 7A in which an handle is retracted.
Figure 7B:
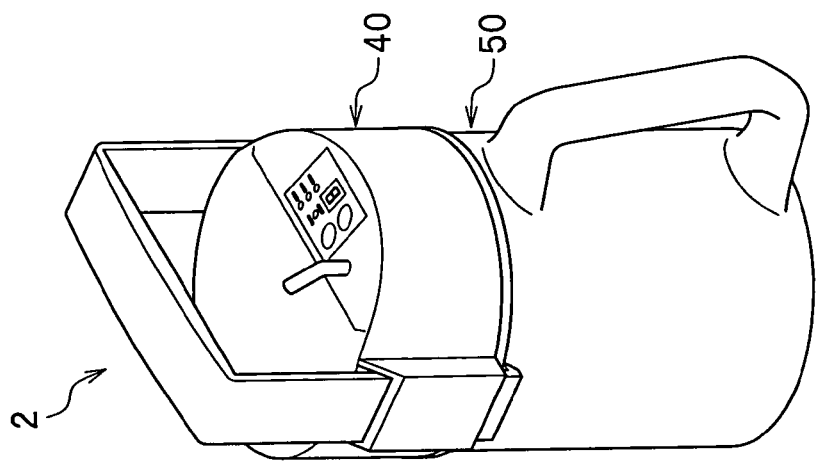
FIG. 7B is a perspective view of the automatic urine collecting apparatus shown in FIG. 7A in which a handle is pulled out.
Figure 7A:
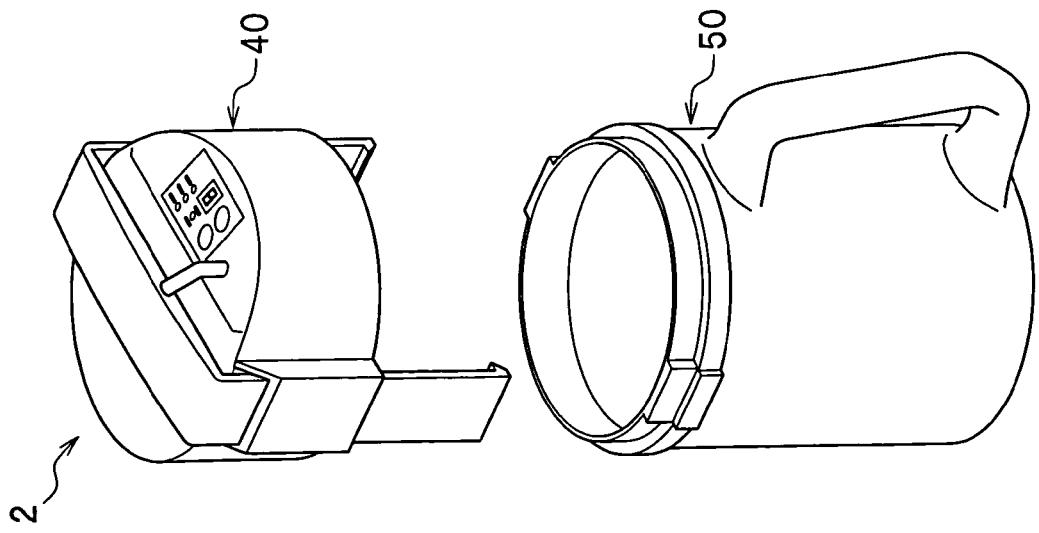
FIG. 7A is an exploded perspective view of an automatic urine collecting apparatus according to a second embodiment.
Figure 8:
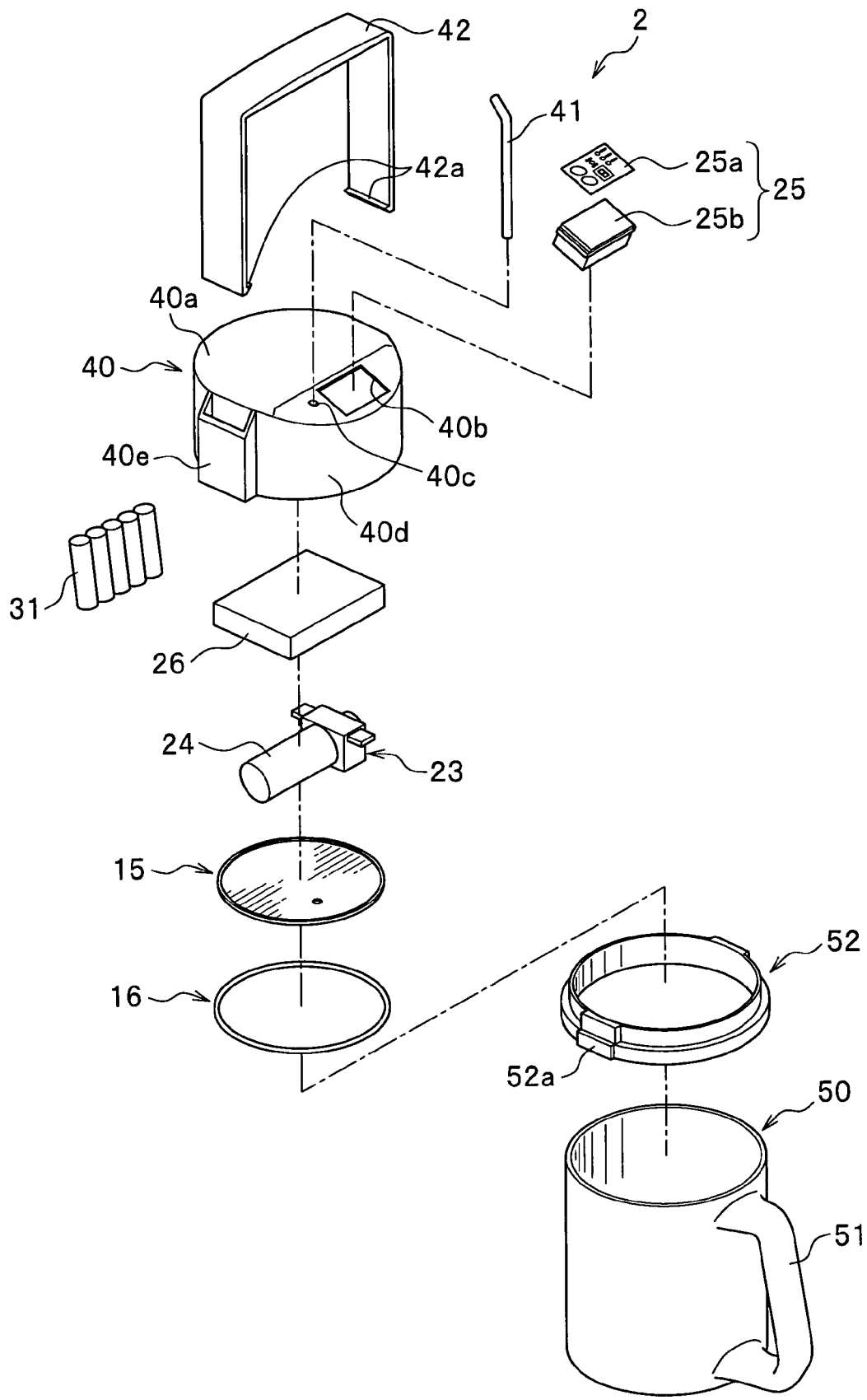
FIG. 8 is an exploded perspective view of the automatic urine collecting apparatus according to the second embodiment.

Hereinafter will be described an automatic urine collecting apparatus 2 according to a second embodiment. In this embodiment, modifying the automatic urine collecting apparatus 1 of the first embodiment provides the automatic urine collecting apparatus 2 of the second embodiment, and thus the same elements as the first embodiment are designated as the same references, omitting their descriptions. FIG. 7A shows the automatic urine collecting apparatus 2 according to the second embodiment, in which a body 40 is detached from a tank 50. FIG. 7B shows a handle 42 of the automatic urine collecting apparatus 2 in a pulled out condition, and FIG. 7C shows the handle in a retracted condition. FIG. 8 shows parts of the automatic urine collecting apparatus 2 shown in FIG. 7A.

As shown in FIGS. 7A to 7C, the automatic urine collecting apparatus 2 is designed to have a body 40 including the function of the lid portion 11 of the first embodiment. The automatic urine collecting apparatus 2 further comprises the tank (collecting container) 50 having a shape that is slightly different from the tank 12. The body 40 and the tank 50 are cup-shaped, in which an opening portion of the tank 50 is detachably attached to the opening of the body 40, wherein the body 40 is coaxially stacked on the tank 50.

As shown in FIG. 8, inside the body 40, the rotary pump 23 and the control circuit board 26 that are the same as those of the first embodiment (not in size) are laterally arranged, respectively, and batteries 31 are contained. The rotary pump 23 (see FIG. 4) is fixed to the body 40 through the vibration absorber 24 so that the sucking inlet 23a downwardly extends. In other words, according to the structure of this embodiment, the rotary pump 23 directly sucks air in the tank 50 without intervening by the connecting pipe 21f and the suction pipe 14 that were used in the first embodiment.

At an open end of the body 40, the gas-liquid separation filter 15 and the O ring 16 that are the same as those in the first embodiment are fixed as mentioned above (see FIG. 3). Further, an upper wall 40a of the body 40 is formed so as to be inclined from the horizon and has a mounting hole 40b, for allowing the indication panel 25 to be inserted and fixed, which is the same as that of the first embodiment. Further the upper wall 40a has a pipe mounting hole 40c for allowing the approximately L-shaped collecting pipe 41 to be inserted and fixed. The collecting pipe 41 is formed to extend from a place above the body 40 to the inside of the tank 50 through the pipe mounting hole 40c and a through hole in the gas-liquid separation filter 15 as shown in FIG. 8.

Formed on outer circumference wall 40d of the body 40 are supporters 40e for slidingly supporting the handle 42 which is formed in a substantially U-shape. Formed at both ends of the handle 42 are catches 42a that inwardly protrude.

Formed integrally on a side surface of the tank 50 is a handle 51. Further, an edge of the tank 50 is fit into an upper edge forming member 52 having a substantially the same shape as the upper edge forming member 17 of the first embodiment. In addition, unlike the upper edge forming member 17 of the first embodiment catches 52a engageable with catches 42a of the handle 42 are formed on the upper edge forming member 52.

According to the second embodiments, forming the body 40 as the lid for the tank 50 can miniaturize the whole size of the automatic urine collecting apparatus 2. Further, the configuration according to this embodiment is provided to directly suck the air in the tank 50 with the rotary pump 23, reducing the number of parts.

Since the upper wall 40a of the body 40 having the indication panel 25 is configured slantingly, the attendant can watch the indication panel 25 only by downwardly casting look at the indication panel 25 without moving to a location above the indication panel 25.

Third Embodiment

Figure 9:
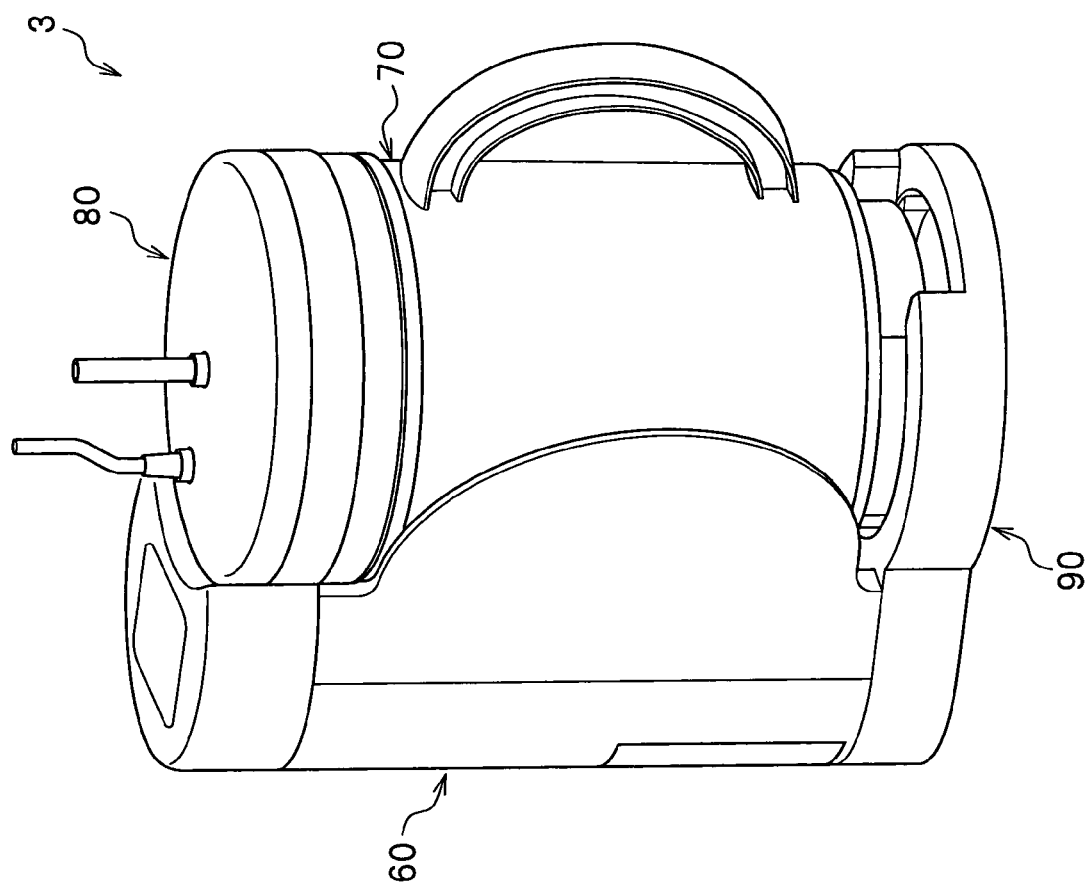
FIG. 9 is a perspective view of an automatic urine collecting apparatus according to a third embodiment.
Figure 10:
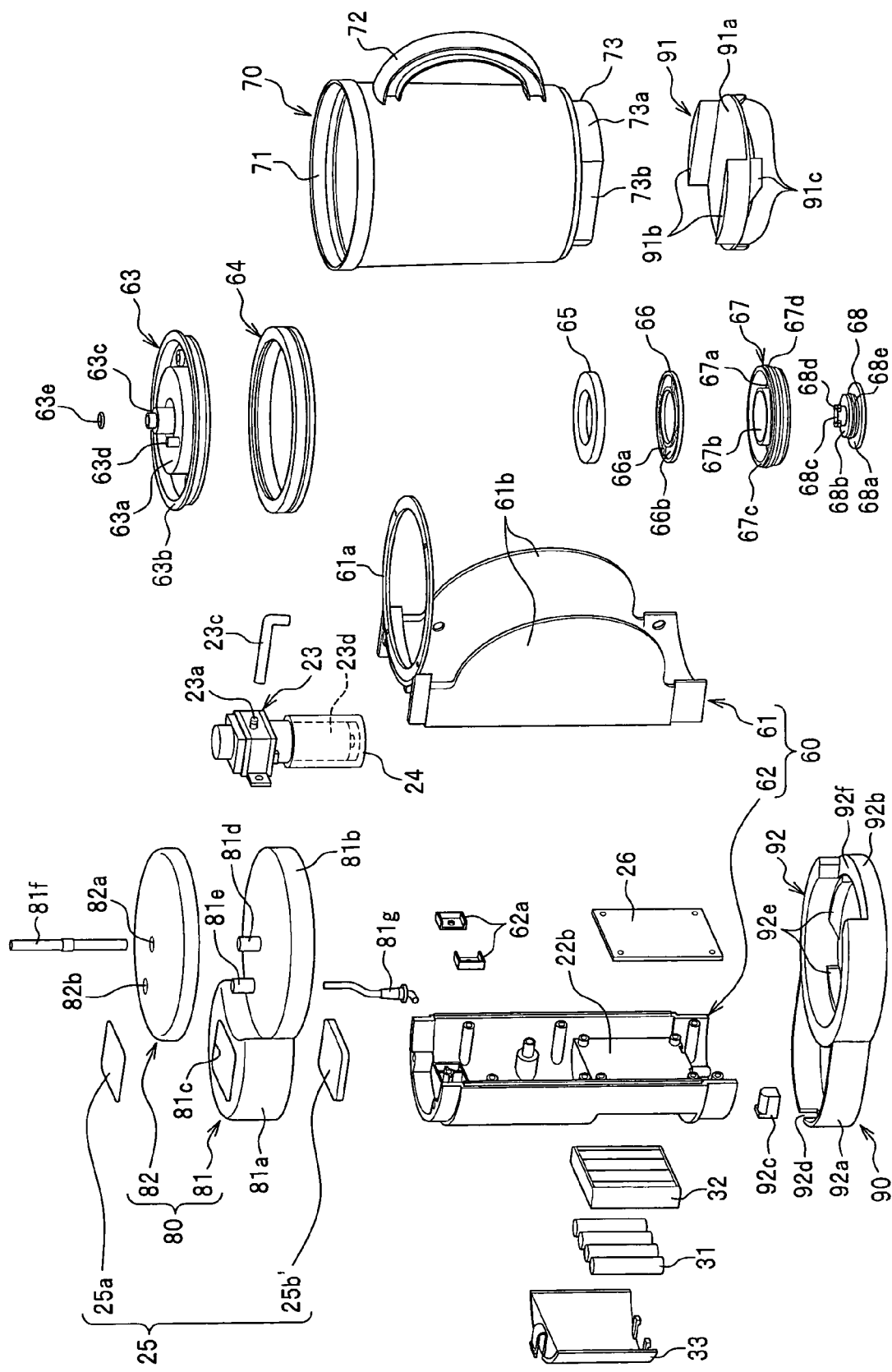
FIG. 10 is a perspective view of an automatic urine collecting apparatus according to the third embodiment.
Figure 11:
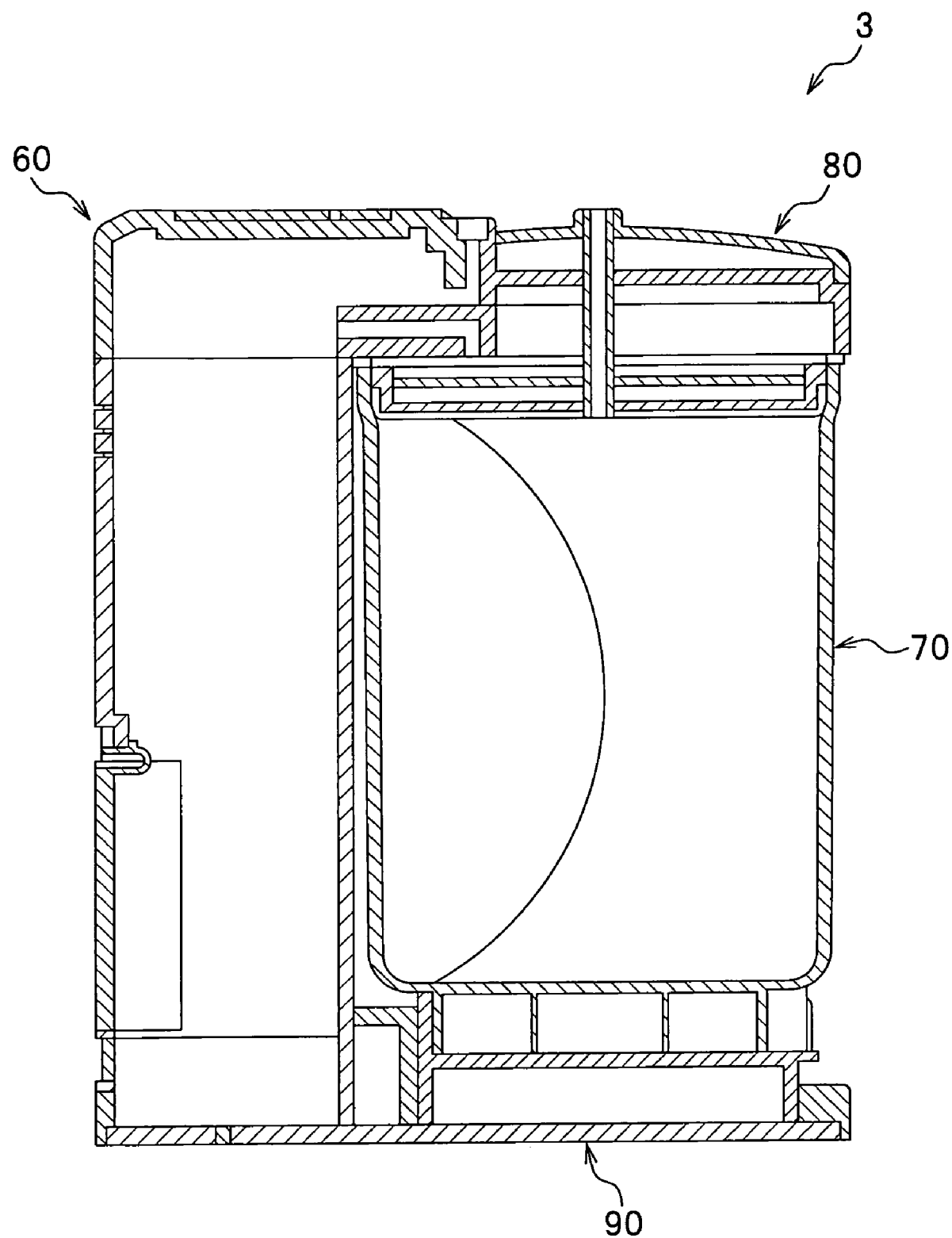
FIG. 11 is a sectional drawing of the automatic urine collecting apparatus according to the third embodiment.

Will be described a third embodiment according to the present invention. This embodiment is provided by modifying the automatic urine collecting apparatus 1 according to the first embodiment, and thus the same elements as the first embodiment are designated as the same references, omitting their descriptions. FIG. 9 shows an automatic urine collecting apparatus 3 according to the third embodiment. FIG. 10 shows parts of the automatic urine collecting apparatus 3. FIG. 11 shows an inner structure of the automatic urine collecting apparatus 3.

As shown in FIG. 9, the automatic urine collecting apparatus 3 comprises a body 60, a tank 70, a shared lid 80 serving as lids for the body 60 and the tank 70, and an elevation mechanism 90 for elevating the tank 70.

As shown in FIG. 10, the body 60 is divided into a front side half 61 and a rear side half 62 and contains the rotary pump 23 (including a vibration absorber 24) and the control circuit board 26 inside them.

Formed at an upper portion of the front side half 61 are a ring base 61a for supporting the filter holder 63 mentioned later and a packing 64. In addition, tank holding portion 61b for preventing the tank 70 from falling down by pinching the tank 70 at the front side (the side of the tank 70).

The filter holder 63 mainly comprises a base 63a formed in substantially a hat shape, a flange 63b extending from the outer peripheral thereof upwardly and then outwardly like an L-shape in cross-section. The flange 63b is fixed to an upper surface of the base 61a. Provided on the upper surface of the base 63a are a pipe guide 63c formed in a sleeve upwardly extending from the center of the base 63a and a pipe connecting opening 63d upwardly extending at a suitable location of the base 63a. The pipe guide portion 63c is stepwise tapered to provide a small diameter portion at an end thereof. Attachment of an O ring 63e to the small-diameter portion and fitting them into a collecting pipe connecting portion 81d of the shared lid 80 mentioned later prevents invasion of air in the tank 70 through the fitting portion. Inside the base 63a are fixed a deodorant filter 65, a gas-liquid separation filter 66, and a filter supporter 67 are fixed with a cap 68.

The deodorant filter 65 is a sponge-like filter absorbing order of the urine collected in the tank 70 and formed in a ring.

The gas-liquid separation filter 66 comprises a base portion 66a annually formed and a gas-liquid separation membrane 66b adhered so as to close a plurality of holes formed along a circumference direction of the base portion 66a.

The filter supporter 67 is a member formed to have flanges 67b and 67c upwardly extending from an inner edge and an outer peripheral edge, of the annular bottom wall 67a to containing the gas-liquid separation filter 66 and the deodorant filter 65 within the recess formed between the two flanges 67b and 67c. In the bottom wall 67a of the filter supporter 67 are formed a plurality of not-shown holes (for example, holes having the same configurations as the holes in the gas-liquid separation filter 66) which allow the pipe connecting opening 63d to suck the air in the tank 70 through the gas-liquid separation filter 66 and the deodorant filter 65. Further, formed at an outer circumferential surface (flange 67c) of the filter supporter 67 is a recess portion in which an O ring 67d is fixed. In this condition, the filter supporter 67 is fit into the base 63a (the sleeve portion with a bottom) to prevent air from invading between the outer circumferential surface of the filter supporter 67 and an inner circumferential surface of the base 63a of the filter holder 63.

The cap 68 comprises a grip 68a formed in a disk and an protruding portion 68b upwardly protruding from the middle of the grip 68a. The protruding portion 68b is formed to have a smaller-diameter at an upper portion thereof and has on its outer circumferential surface, a catch 68d for catching an engaging portion (not shown) provided at an inner surface of the filter holder 63. After the filter supporter 67 is fit into the filter holder 63 and then the cap 68 is pushed into the filter supporter 67 along its inner circumferential surface, rotation of the cap 68 catches the engaging portion in the filter holder 63 to be fixed to the filter holder 63. The cap 68 fixed to the filter holder 63 as mentioned above functions as a stopper for preventing the filter supporter 67 from detaching. In addition, formed on an outer circumferential surface of the protruding portion 68b of the cap 68 is a recess portion in which an O ring 68e is fit. In this condition, the cap 68 is fit in an inner circumferential surface of the filter supporter 67 to prevent air from invading between an outer circumferential surface of the protruding portion 68b of the cap 68d and an inner circumferential surface of the filter supporter 67.

A packing 64 is a member made of rubber annularly formed and fixed to an under surface of the base 61a of the front side half 61. The packing 64 is formed to have an outer diameter slightly larger an inner diameter of the upper inside edge of the tank 70 (an upper edge forming member 71 mentioned later) to bring it in tight contact with the upper inside edge of the tank 70. Here, because the tank 70 ascends as it rotates (mentioned later), the packing 64 rubs against the tank 70 when the packing 64 brings in tight contact with the tank 70. Thus, preferably, a material with a high endurance is selected for the packing 64.

The rear side half 62 is formed in a substantially half pipe. Formed at a back side of the rear side half 62 is the battery box 22b like the first embodiment. The battery box 22b is provided with the dry batteries 31, the electrical connecting portion 32, and the cover 33. Further, an upper portion (the pump mechanism at the upper side) of the rotary pump 23 is fixed to the inside of the rear side half 62. The sucking inlet 23a of the rotary pump 23, fixed as mentioned above, is connected to an end of the L-shaped suction pipe 23c. The other end of the suction pipe 23c is connected to the pipe connection opening 63d of the filter holder 63. The motor portion 23d at the lower side of the rotary pump 23 is fixed to a side wall of the body 60 (front side half 61) through the vibration absorber 24 like the first embodiment. In the third embodiment, both the upper portion and the lower portion (motor portion 23d) of the rotary pump 23 are fixed to the body 60 through the elastic material. However, the present invention is not limited to this and thus, only the motor portion 23d may be fixed to the body 60 through the vibration absorber 24 like the first embodiment.

The tank 70 is cup-shaped and has, at an opening edge, an upper edge forming member 71 of which upper end is outwardly depressed with a step and a handle 72 integrally formed on a side surface of the tank 70. Formed on a lower surface of the tank 70 is an engage portion 73 for engaging with a rotary elevating platform 91 without relative rotation.

The shared lid 80 comprises a base 81 and a transparent lid 82. The base 81 comprises a cup-shaped body-side lid 81a and a cup-shaped tank lid 81b.

The body-side lid 81a is formed to be fit into a rear side part of an upper portion of the front side half 61 and an upper portion of the rear side half 62 and to have, at an upper surface thereof, a mounting hole 81c for mounting the indication panel 25. A switch circuit board 25b' according to this embodiment is different from that of the first embodiment because it is formed in a plate, but its function is the same as that of the first embodiment. In addition, the upper wall of the body side lid 81a is formed to be inclined from the horizontal. This makes it easier to watch the indication panel 25 and prevents a child or the like from putting something on the apparatus.

The tank lid 81b is formed lower than the body-side lid 81b stepwise and formed to have a depth sufficient for covering the filter holder 63 and the packing 64. Formed on an upper wall of the tank lid 81b are a sleeve collecting pipe connection portion 81d upwardly protruding from the middle of the upper wall and a sleeve cable inlet 81e upwardly protruding from a portion near the body-side lid 81a. Connected to the collecting pipe connection portion 81d is a collecting pipe 81f for guiding the urine flowing through the tube T (see FIG. 1) to the tank 70. In addition, a cable 81g for connection between the sensors S1 and S2 (see FIG. 1) and the control circuit board 26 is inserted in the cable inlet 81e.

The transparent lid 82 is detachably attached to the tank lid 81b, an upper wall of which has holes 82a and 82b to provide clearance for the collecting pipe connection portion 81d and the cable inlet 81e. Arrangement of the transparent lid 82 detachable from the tank lid 81b allows the attendant to wash only the transparent lid 82 removed from the shared lid 80 although the urine drops from the collecting pipe 81f when the collecting pipe 81f is removed from the shared lid 80 to clean the collecting pipe 1. Further, the upper surface of the transparent lid 82 is formed in a spherical surface portion, in which a center thereof corresponds to a vertex of the spherical portion. This prevents a child or the like from putting something thereon.

The elevation mechanism 90 comprises the rotary elevating platform 91 and a base 92 for supporting the rotary elevating platform 91 with rotation and elevation.

The elevation platform 91 comprises a mounting plate 91a formed in a disk, a pair of rotation supporters 91b formed on an upper surface of the mounting plate 91a, and four elevation legs 91c formed on a lower surface of the mounting plate 91a (only three are shown).

The rotary supporters 91b are formed so as to face each other across a center of the mounting plane 91a to engage the engage portion 73 without relative rotation movement. The engage portion 73 is formed to have two curved walls 73a along an outer circumference of the mounting plate 91a and two flat surface portions 73b (only one is shown) formed in parallel with inner surfaces of the rotary supporters 91b, respectively.

The elevation legs 91c is formed in a rectangular plate cured along the outer circumference of the mounting plate 91a, wherein one of two sides (edges) facing to each other in the circumferential direction thereof is formed slantwise and the other side is vertical. The four elevation legs 91c are equidistantly arranged in the circumferential direction.

The base 92 comprises a platform housing portion 92b for housing the rotary elevation platform 91.

The body mounting portion 92a is cup-shaped in which a mounting groove 92d is formed to mount an adapter connection portion 92c. To avoid interference with the adapter connection portion 92c, a groove and a hole are formed at a lower portion of the rear side half 62.

An elevation mechanism will be described.

The platform housing portion 92b is formed in a sleeve with a bottom and formed to have four cam supports 92e (only two are shown) for engaging with the elevation legs 91c. The cam supports 92e are formed so as to fill the spaces formed between any of two of consecutive elevation legs 91c. According to this structure, when each of the elevation legs 91c locates between the cam supports 92e, the tank 70 on the rotary elevation platform 91 is placed at the lowest position. Clockwise rotation of the rotary elevation platform 91 with the tank 70 from that condition elevates the rotary elevation platform 91 along the slope of the cam supports 92e. When the elevation legs 91c mount on upper surfaces of the cam supports 92e, it is placed at the uppermost position.

Formed at a part of a side wall of the platform housing portion 92b is an insertion opening 92f for allowing the tank 70 to enter the space provided by the rotary elevation platform 91 (the space formed by a pair of the rotary supporters 91b and the platform 91a) as the tank 70 is slid. Thus, clockwise rotation of the tank 70 after inserting it through the insertion opening 92f elevates the tank 70, making the opening of the tank 70 in tight contact with the packing 64 to collect the urine. To discard the urine, counterclockwise rotation of the tank 70 in tight contact with the packing 64 and then drawing the tank 70 through the insertion opening 92f permits removal of the tank 70 from the apparatus.

More specifically, when the tank 70 enters the space provided by the rotary elevation platform 91 as the tank 70 is slid, the tank 70 engages with the rotary elevation platform 91. The tank 70 has, at a bottom thereof, the two flat surface portions 73b as a first engage member. The rotary supporters 91b as a second engage member engageable with the flat surface portions 73b which transmits rotation movement of the container to the rotary supporters 91b, and the elevation mechanism converts the rotation movement received by the rotary supporters 91b to an upward movement to elevate the container.

Accordingly, the elevation legs 91c includes the (first) slope and connected to the rotary supporters 91b, the cam support 92e supported by the platform housing portion 92b and including a (second) slope that is slidingly in contact with the first slope, and a structure for coaxially rotating the rotary elevation platform 91 and the base 92, and wherein the rotation movement received by the rotary elevation platform 91 rotates the first slope that climbs the second slope to elevate the container 70.

As mentioned above, according to the third embodiment, setting is simply provided by rotating the tank 70 after insertion of the tank 70 into the elevation mechanism 90. Further, removal of the tank 70 can be provided only by rotating the tank 70 counterclockwise and drawing it.

Slantwise form of the upper wall of the body-side lid 81a and spherical shape of the upper surface of the transparent lid 82 inhibits a child or the like from putting something on the apparatus, so that the apparatus can be protected from heavy weight of the things placed on the apparatus.

It is sufficient to prepare the gas-liquid separation membrane 66b used for the gas-liquid separation filter 66 with a length sufficient to cover a thin hole formed in the annular base 66a with a small amount of the gas-liquid separation membrane 66b that is expensive, so that the cost can be reduced.

In the embodiments, the rotary pump 23 generates a reduced-pressure to suck and convey urine from the urine receiver R to the container 12 (50, 70) through the tube T and the container 12 (50, 70), wherein the rotary pump 23, the container 12 (50, 70), and the tube T and the receiver R are hermetically sealed. The automatic urine collecting apparatus 1 (2, 3) further comprises the gas-liquid separating filter 15 and the guide pipe 21d of which one end is connectable to the tube, an end of the collecting tube 13 connected to the guide tube 21d being located at a first level in the container, wherein the suction pipe 14 connected to the rotary pump 23 is located at a second level in the container higher than the first level, and the gas-liquid separating filter 15 is located between the first and second levels and hermetically sealed regarding spaces at upper side 11e and lower side thereof.

The invention claimed is:

1. An automatic urine collecting apparatus for collecting urine received by a urine receiver through a tube, the apparatus comprising:
   a container for receiving and storing urine;
   a rotary pump adapted to generate a reduced pressure to suck and convey urine from the urine receiver to the container through the tube;
   a body containing the rotary pump; and
   an attachment mechanism for detachably attaching the container to the body,
   wherein the container is cup-shaped,
   wherein the body comprises an overhead portion arranged to cover and be hermetically connected to an opening of the container, and a stand supporting the overhead portion and the container; and
   wherein the stand comprises an elevation mechanism for elevating the container when the container is placed on the stand until the opening of the container is hermetically connected to the overhead portion.

2. The automatic urine collecting apparatus as claimed in claim 1, further comprising an attachment structure for detachably attaching aholder holding an absorbing agent for absorbing the urine to the container.

3. The automatic urine collecting apparatus as claimed in claim 1, wherein the body comprises a hermetical chamber coupled to the pump and hermetically connected to an upper portion of the container to suck air above the urine in the container when the urine is partially stored in the container.

4. The automatic urine collecting apparatus as claimed in claim 3, further comprising a gas-liquid separating filter between the chamber and the container for allowing the air in the container to pass therethrough.

5. The automatic urine collecting apparatus as claimed in claim 1, wherein the stand comprises a catching mechanism for detachably catching the container at a side surface of the stand.

6. The automatic urine collecting apparatus as claimed in claim 1, wherein the stand has a base for detachably catching the container at a bottom of the container, and the base comprises the elevation mechanism.

7. The automatic urine collecting apparatus as claimed in claim 1, wherein the container comprises, at a bottom thereof, a first engage member, the elevation mechanism comprising a second engage member engageable with the first engage member which transmits rotation movement of the container to the second engage member, and the elevation mechanism converts the rotation movement received by the second engage member to an upward movement to elevate the container.

8. The automatic urine collecting apparatus as claimed in claim 7, wherein the elevation mechanism further comprises a base plate, a first member including a first slope and connected to the second engage member, a second member supported by the base plate and including a second slope that is slidingly in contact with the first slope, and a structure for coaxially rotating the first and second members, and wherein the rotation movement received by the second engage member rotates the first slope that climbs the second slope to elevate the container.

9. The automatic urine collecting apparatus as claimed in claim 1,
   Wherein the container comprises a handle for gripe to carry the container.

10. The automatic urine collecting apparatus as claimed in claim 1, further comprising:
    an elastic material;
    wherein the rotary pump comprises a motor portion; and
    wherein the motor portion is fixed to the body through the elastic material.

11. The automatic urine collecting apparatus as claimed in claim 1, further comprising:
    a U-shaped handle for carrying the body and the container, wherein the body comprises slide mechanisms for slidingly supporting end bars of the handle, respectively, and the container comprises catch mechanisms for catching ends of the end bars, respectively, in order to allow the handle to be in an extended position and a retracted position.

12. The automatic urine collecting apparatus as claimed in claim 1, further comprising an indication panel for indicating information that prompts a user to discard the urine stored in the container.

* * * * *